US011906499B2

United States Patent
Wang et al.

(10) Patent No.: US 11,906,499 B2
(45) Date of Patent: Feb. 20, 2024

(54) SYSTEM AND METHOD FOR ANALYZING VOLATILE COMPONENT IN EXTRATERRESTRIAL SOIL THROUGH PENETRATION HEATING INDUCTION

(71) Applicant: Sichuan Institute of Space Systems Engineering, Chengdu (CN)

(72) Inventors: Xinjian Wang, Chengdu (CN); Yubin Yang, Chengdu (CN); Yi Zuo, Chengdu (CN); Cheng Qian, Chengdu (CN); Yuehai Chen, Chengdu (CN); Lisheng Deng, Chengdu (CN); Xiandong Nie, Chengdu (CN); Yunyun Guo, Chengdu (CN); Jin Liu, Chengdu (CN); Yu Luo, Chengdu (CN); Hansheng Zheng, Chengdu (CN)

(73) Assignee: SICHUAN INSTITUTE OF SPACE SYSTEMS ENGINEERING, Chengdu (CN)

( * ) Notice: Subject to any disclaimer, the term of this patent is extended or adjusted under 35 U.S.C. 154(b) by 0 days.

(21) Appl. No.: 17/457,259

(22) Filed: Dec. 2, 2021

(65) Prior Publication Data

US 2023/0060607 A1  Mar. 2, 2023

(30) Foreign Application Priority Data

Aug. 26, 2021 (CN) .......................... 202110989081.2

(51) Int. Cl.
*G01N 33/24* (2006.01)
*G01N 1/44* (2006.01)

(52) U.S. Cl.
CPC ............... *G01N 33/24* (2013.01); *G01N 1/44* (2013.01); *G01N 2033/243* (2013.01)

(58) Field of Classification Search
CPC ..... G01N 1/44; G01N 33/24; G01N 2033/243
(Continued)

(56) References Cited

U.S. PATENT DOCUMENTS

| 2,849,970 A | * | 9/1958 | Coberly | ............... A01C 23/025 |
| | | | | 111/119 |
| 4,335,622 A | * | 6/1982 | Bartz | ................... G01N 1/2294 |
| | | | | 175/21 |

(Continued)

FOREIGN PATENT DOCUMENTS

| CN | 101858075 B | * | 1/2012 | |
| CN | 105021660 B | * | 11/2017 | |
| CN | 110512584 A | * | 11/2019 | ............. E02D 1/022 |

OTHER PUBLICATIONS

Humayan "Analyzing Volatile Chemicals in the Moon's Dark Craters," American Geophysical Union (Year: 2020).*
(Continued)

*Primary Examiner* — John Fitzgerald
(74) *Attorney, Agent, or Firm* — Bayramoglu Law Offices LLC

(57) ABSTRACT

A system for analyzing a volatile component in extraterrestrial soil through penetration heating induction includes the following: a penetration heater, provided therein with a volatile component measurement and analysis module configured to analyze a volatile component in a detected medium; a gas capture hole, provided on a side wall of the penetration heater and used to divert the volatile component in the detected medium to the volatile component measurement and analysis module; a temperature acquisition module, disposed on the penetration heater and configured to acquire a temperature of the detected medium; and a heating module, disposed on the penetration heater and configured to acquire the temperature of the detected medium. The system has a compact structure, a simple function, and low (Continued)

engineering costs, and can directly detect and analyze a volatile component in deep extraterrestrial soil.

5 Claims, 2 Drawing Sheets

(58) Field of Classification Search
USPC .......................................... 73/863.11; 175/17
See application file for complete search history.

(56) References Cited

U.S. PATENT DOCUMENTS

| | | | | |
|---|---|---|---|---|
| 4,452,091 A | * | 6/1984 | Richers | G01V 9/007 |
| | | | | 73/864.74 |
| 4,809,790 A | * | 3/1989 | Manchak, Jr. | E21B 10/04 |
| | | | | 175/46 |
| 5,150,622 A | * | 9/1992 | Vollweiler | G01N 1/2294 |
| | | | | 175/21 |
| 5,337,838 A | * | 8/1994 | Sorensen | E21B 49/08 |
| | | | | 175/309 |
| 5,411,087 A | * | 5/1995 | Taylor | E21B 49/084 |
| | | | | 166/264 |
| 5,461,229 A | * | 10/1995 | Sauter | G01N 33/24 |
| | | | | 250/341.2 |
| 5,587,538 A | * | 12/1996 | Bratton | G01N 1/14 |
| | | | | 73/863.33 |
| 5,635,710 A | * | 6/1997 | Reed | E21B 47/017 |
| | | | | 250/374 |
| 5,744,730 A | * | 4/1998 | Ballard | E21B 49/081 |
| | | | | 175/50 |
| 5,902,939 A | * | 5/1999 | Ballard | E21B 49/081 |
| | | | | 73/864.81 |
| 6,487,920 B1 | * | 12/2002 | Robbat, Jr. | E21B 7/26 |
| | | | | 73/864.74 |
| 7,723,654 B2 | * | 5/2010 | Taylor | E01C 21/02 |
| | | | | 219/679 |
| 8,074,490 B2 | * | 12/2011 | Andrews, Jr. | G01N 1/2294 |
| | | | | 73/31.05 |
| 2004/0069046 A1 | * | 4/2004 | Sunshine | G01N 33/0009 |
| | | | | 422/90 |
| 2008/0003133 A1 | * | 1/2008 | Taylor | B64G 99/00 |
| | | | | 422/21 |

OTHER PUBLICATIONS

Kate et al. "VAPoR—Volatile Analysis by Pyrolysis of Regolith—an instrument for in situ detection of water, noble gases, and organics on the Moon," Planetary and Space Science 58 (2010) 1007-1017 (Year: 2010).*

* cited by examiner

SYSTEM AND METHOD FOR ANALYZING VOLATILE COMPONENT IN EXTRATERRESTRIAL SOIL THROUGH PENETRATION HEATING INDUCTION

CROSS REFERENCE TO THE RELATED APPLICATIONS

This application is based upon and claims priority to Chinese Patent Application No. 202110989081.2, filed on Aug. 26, 2021, the entire contents of which are incorporated herein by reference.

TECHNICAL FIELD

The present disclosure relates to the technical field of in-situ penetration detection for celestial bodies, and specifically, to a system and method for analyzing a volatile component in extraterrestrial soil through penetration heating induction.

BACKGROUND

For the study of celestial bodies, isotopic analysis is performed on volatile components and gas to obtain distribution information of celestial resources and to study whether the celestial bodies have or can provide basic material conditions for biological existence. In addition, the study of the volatile components can reveal a history of specific major geological events, deduce origins and early formation processes of the celestial bodies, and explain the origins and evolution of the celestial bodies. The study of a volatile component in lunar soil can provide valuable information for the evolution of the solar system.

Because volatile components are temperature-dependent and are volatile, the in-situ study of the volatile components is the most accurate and valuable. At present, the in-situ sampling and heating method is typically used for the in-situ detection of volatile components at home and abroad. For example, in the Artemis program of the United States, a drill is used to drill into a specific depth of the lunar soil, the acquired lunar soil is transferred to a heating furnace for heating, and mass and optical spectrum analysis is performed on a volatile component generated after heating. In the Luna-27 program of Russia, a drill is also used to drill into the lunar soil for in-situ sampling, where the samples are put in a plurality of sample boxes, a sealed heating is performed on the samples, and a volatile component analysis is performed on the samples obtained after sealed heating. The foregoing methods all have disturbance and an impact of drilling heat on the volatile component in the lunar soil, and thus it is difficult to obtain and analyze the temperature-sensitive volatile component. In addition, the drill is heavy and has high power consumption.

SUMMARY

The present disclosure provides a system and method for analyzing a volatile component in extraterrestrial soil through penetration heating induction. A release of a volatile component is induced through penetration frictional heating, and a volatile component detection and analysis apparatus integrated in a penetration heater is used to directly analyze the volatile component. In this way, the temperature-sensitive volatile component can be directly analyzed in a penetration region. The system has great scientific value, a compact structure, a low weight, and low costs.

To achieve the foregoing objective, the present disclosure adopts the following technical solutions:

A system for analyzing a volatile component in extraterrestrial soil through penetration heating induction is provided, including: a penetration heater, provided therein with a volatile component measurement and analysis module configured to analyze a volatile component in a detected medium; a gas capture hole, provided on a side wall of the penetration heater and used to divert the volatile component in the detected medium to the volatile component measurement and analysis module; a temperature acquisition module, disposed on the penetration heater and configured to acquire a temperature of the detected medium; and a heating module, disposed on the penetration heater and configured to acquire the temperature of the detected medium.

In some embodiments, the gas capture hole provided on the side wall of the penetration heater may be annular.

In some embodiments, the penetration heater may be provided with a plurality of annular gas capture holes.

In some embodiments, the annular gas capture holes may be arranged at equal intervals.

In some embodiments, a blocking member is disposed on a side of each gas capture hole close to a tip of the penetration heater.

An embodiment further provides a method for analyzing a volatile component in extraterrestrial soil through penetration heating induction, including the following steps:
step 1: quickly penetrating, by a penetration heater, a detected medium with help of penetrating kinetic energy, where frictional heating, thermal energy released from the penetration heater and a temperature of the detected medium induce a release of a volatile component in the detected medium; and
step 2: entering, by the induced volatile component, a volatile component measurement and analysis module through a gas capture hole, and performing in-situ analysis on the volatile component.

In some embodiments, in step 1, the thermal energy released from the penetration heater and the temperature of the detected medium may be provided and controlled by a heating module.

In some embodiments, in a process of inducing the release of the volatile component in the detected medium in step 1, the heating module may be used to perform temperature compensation and continuous heating to improve release efficiency of the volatile component.

In some embodiments, in step 2, after the temperature decreases, the detected medium may be cyclically heated by the heating module to improve analysis accuracy of the volatile component in the penetrated detected medium.

Figure 1:
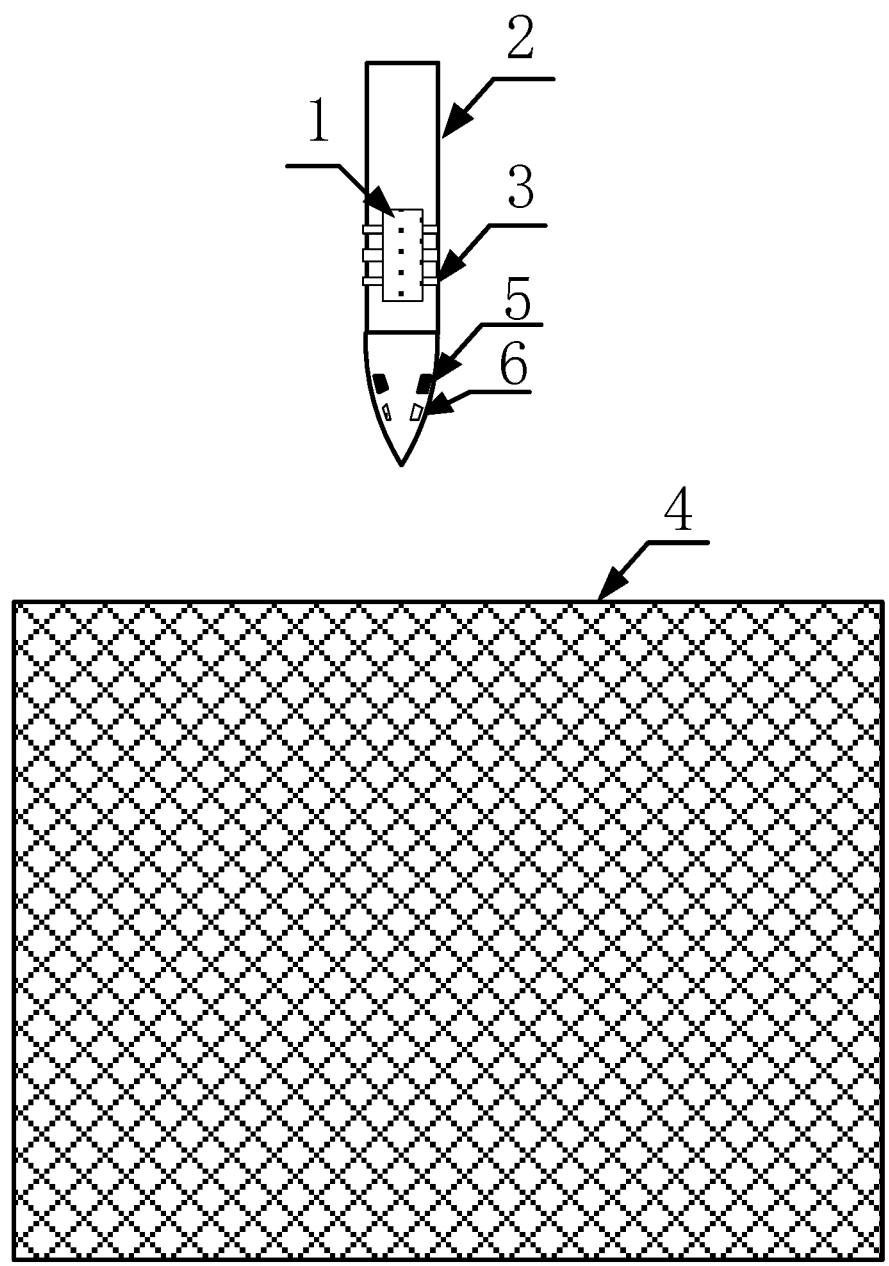
FIG. 1 is a schematic diagram of a system for analyzing a volatile component in extraterrestrial soil through penetration heating induction and a detected medium before penetration according to an embodiment of the present disclosure.

Reference numerals in the figures: 1—volatile component measurement and analysis module, 2—penetration heater, 3—gas capture hole, 4—detected medium, 5—temperature acquisition module, 6—heating module, and 7—volatile component.

DETAILED DESCRIPTION OF THE EMBODIMENTS

To make the objectives, technical solutions, and advantages of the present disclosure clearer, the present disclosure is further described in detail below with reference to the accompanying drawings and embodiments. It should be understood that the specific embodiments described herein are merely intended to explain the present application, rather than to limit the present application.

Instead, the present application is attached to any substitutions, modifications, equivalent methods and solutions defined by the claims in the spirit and scope of the present application. Further, for better understanding of the present application, in the following detailed description of the present application, some specific details are described in detail. Those skilled in the art can fully understand the present application without the description of these details.

Figure 2:
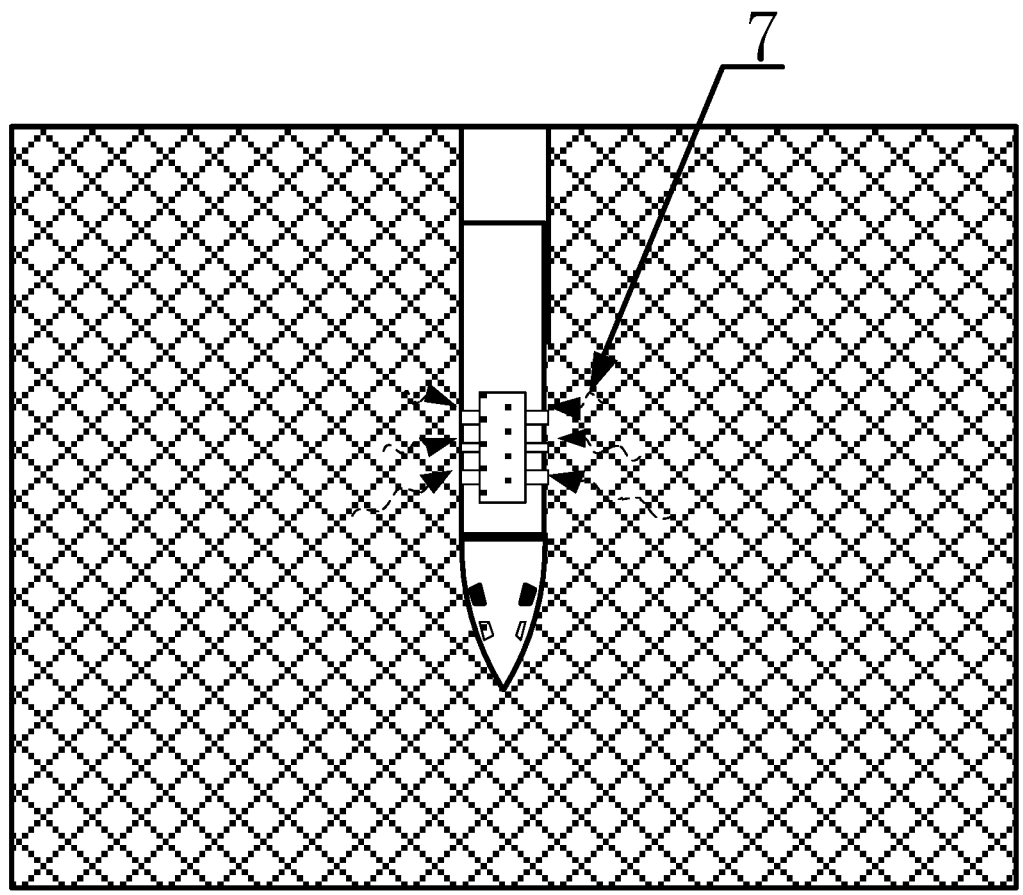
FIG. 2 is a schematic diagram of a system for analyzing a volatile component in extraterrestrial soil through penetration heating induction and a detected medium after penetration according to an embodiment of the present disclosure.

The following describes a system and method for analyzing a volatile component in extraterrestrial soil through penetration heating induction involved in the embodiments of the present application in detail with reference to FIG. 1 and FIG. 2. It should be noted that the following embodiments are merely used to explain the present application and do not constitute a limitation to the present application.

In an embodiment of the present application, as shown in FIG. 1 and FIG. 2, a system for analyzing a volatile component in extraterrestrial soil 7 through penetration heating induction includes a volatile component 7 measurement and analysis module 1, a gas capture hole 3, a temperature acquisition module 5, and a heating module 6. The volatile component 7 measurement and analysis module 1 is disposed inside a penetration heater 2 and configured to analyze a volatile component 7 in a detected medium 4. The gas capture hole 3 is provided on a side wall of the penetration heater 2 and used to divert the volatile component 7 in the detected medium 4 to the volatile component 7 measurement and analysis module 1. The temperature acquisition module 5 is disposed on the penetration heater 2 and configured to acquire a temperature of the detected medium 4. The heating module 6 is disposed on the penetration heater 2 and configured to acquire the temperature of the detected medium 4.

As shown in FIG. 1, the penetration heater 2 quickly penetrates the detected medium with help of penetrating kinetic energy or the like. Frictional heating, the thermal energy released from the penetration heater and a temperature of the detected medium induce a release of the volatile component 7 in the detected medium 4. An induction temperature of the volatile component 7 is acquired by the temperature acquisition module 5 for testing. During the induction, the heating module 6 may further be used to perform temperature compensation and continuous heating to improve release efficiency of the volatile component 7.

The induced volatile component 7 enters the volatile component 7 measurement and analysis module 1 through the gas capture hole 3, and in-situ analysis is performed on the volatile component to directly identify the volatile component 7 in lunar soil. After the temperature decreases, the detected medium 4 may be cyclically heated by the heating module 6 to improve analysis accuracy of the volatile component 7 in the penetrated medium.

In some embodiments, the gas capture hole 3 provided on the side wall of the penetration heater 2 may be annular. The penetration heater 2 may be provided with a plurality of annular gas capture holes 3. The annular gas capture holes 3 may be arranged at equal intervals. The gas capture hole 3 is annular to facilitate full capture of the induced volatile component 7 in the circumference of the penetration heater 2, improve capture efficiency, and improve analysis accuracy of the volatile component 7 in the penetrated medium.

In some embodiments, a blocking member is disposed on a side of each gas capture hole 3 close to a tip of the penetration heater 2. The blocking member prevents the detected medium 4 from entering the gas capture hole 3 in large quantities and affecting the capture of the volatile component 7 when the penetration heater 2 penetrates the detected medium 4.

An embodiment further provides a method for analyzing a volatile component 7 of extraterrestrial soil through penetration heating induction, including the following steps:

Step 1: The penetration heater 2 quickly penetrates the detected medium with the help of the kinetic energy. Frictional heating, the thermal energy released from the penetration heater and the temperature of the detected medium induce the release of the volatile component 7 in the detected medium 4.

The thermal energy released from the penetration heater and the temperature of the detected medium may be provided and controlled by the heating module 6. In a process of inducing the release of the volatile component 7 in the detected medium 4, the heating module 6 may be used to perform temperature compensation and continuous heating to improve the release efficiency of the volatile component 7.

Step 2: The induced volatile component 7 enters the volatile component 7 measurement and analysis module 1 through the gas capture hole 3. Perform in-situ analysis on the volatile component. After the temperature decreases, the detected medium 4 may be cyclically heated by the heating module 6 to improve the analysis accuracy of the volatile component 7 in the penetrated detected medium.

After cooling, the detected medium 4 may be heated by the heating module 6. For example, assuming that the temperature of the detected medium 4 is −200° C. after cooling, the heating module 6 may heat the detected medium 4 to 200° C., and the temperature acquisition module 5 acquires the temperature ranging from −200° C. to 200° C. Based on a specific heating rate, the volatile component 7 measurement and analysis module 1 is used to analyze changes and details of the induced volatile component 7 in the detected medium 4 in situ.

The possible beneficial effects of the test apparatus for high-speed deployment of a test cable disclosed in the present application include but are not limited to the following: The present disclosure provides the system and method for analyzing a volatile component in extraterrestrial soil through penetration heating induction. The system and method are used to directly detect and analyze the volatile component in the extraterrestrial soil. The temperature-sensitive volatile component can be directly analyzed in a penetration region. The system has great scientific value, a compact structure, a low weight, and low costs.

The foregoing descriptions are merely preferred embodiments of the present disclosure, and are not intended to limit the present disclosure. Any modification, equivalent substitution, and improvement without departing from the spirit and principle of the present disclosure shall be included within the protection scope of the present disclosure.

What is claimed is:

1. A method for analyzing a volatile component in extraterrestrial soil through penetration heating induction, comprising the following steps:
step 1: penetrating a penetration heater into the extraterrestrial soil with a speed, wherein frictional heat generated from the penetration and a temperature of the penetration heater induce release of a volatile component from the extraterrestrial soil to obtain an induced volatile component; and
step 2: performing in-situ analysis on the induced volatile component, wherein the induced volatile component enters a volatile component measurement and analysis module disposed inside the penetration heater through a plurality of annular gas capture holes provided at equal intervals on a sidewall of the penetration heater for analysis by the volatile component measurement and analysis module,
wherein following a decrease of the temperature of the extraterrestrial soil in step 1 to −200° C., the extraterrestrial soil is cyclically heated to 200° C. by a heating module to improve in-situ analysis accuracy of the induced volatile component in the extraterrestrial soil, and
wherein a temperature acquisition module is disposed on the penetration heater and acquires a temperature of the extraterrestrial soil.

2. The method for analyzing the volatile component in extraterrestrial soil through penetration heating induction according to claim 1, wherein in step 1, the heating module disposed on the penetration heater provides and controls the temperature of the penetration heater.

3. The method for analyzing the volatile component in extraterrestrial soil through penetration heating induction according to claim 1, wherein in a process of inducing the release of the volatile component in the extraterrestrial soil in step 1, the heating module is used to perform temperature compensation and continuous heating to improve release efficiency of the volatile component.

4. The method for analyzing the volatile component in extraterrestrial soil through penetration heating induction according to claim 1, wherein the extraterrestrial soil is lunar soil.

5. The method for analyzing the volatile component in extraterrestrial soil through penetration heating induction according to claim 1, wherein in step 2, performing in-situ analysis on the induced volatile component comprises identifying the induced volatile component in the soil.

* * * * *